(12) United States Patent
Seo

(10) Patent No.: US 12,098,134 B2
(45) Date of Patent: Sep. 24, 2024

(54) BENZO-HETEROCYCLIC COMPOUND AND COMPOSITION FOR PREVENTING OR TREATING CANCER DISEASE, CONTAINING SAME AS ACTIVE INGREDIENT

(71) Applicant: INDUSTRY ACADEMIC COOPERATION FOUNDATION KEIMYUNG UNIVERSITY, Daegu (KR)

(72) Inventor: Young Ho Seo, Daegu (KR)

(73) Assignee: INDUSTRY ACADEMIC COOPERATION FOUNDATION KEIMYUNG UNIVERSITY, Daegu (KR)

(*) Notice: Subject to any disclaimer, the term of this patent is extended or adjusted under 35 U.S.C. 154(b) by 799 days.

(21) Appl. No.: 17/283,950

(22) PCT Filed: Aug. 16, 2019

(86) PCT No.: PCT/KR2019/010443
§ 371 (c)(1),
(2) Date: Apr. 8, 2021

(87) PCT Pub. No.: WO2020/091204
PCT Pub. Date: May 7, 2020

(65) Prior Publication Data
US 2021/0387951 A1    Dec. 16, 2021

(30) Foreign Application Priority Data

Oct. 30, 2018  (KR) .................. 10-2018-0130668

(51) Int. Cl.
| | | |
|---|---|---|
| C07D 235/12 | (2006.01) | |
| A23L 33/00 | (2016.01) | |
| A23L 33/10 | (2016.01) | |
| A61P 35/00 | (2006.01) | |
| C07D 263/57 | (2006.01) | |
| C07D 277/66 | (2006.01) | |

(52) U.S. Cl.
CPC ............ *C07D 235/12* (2013.01); *A23L 33/10* (2016.08); *A23L 33/30* (2016.08); *A61P 35/00* (2018.01); *C07D 263/57* (2013.01); *C07D 277/66* (2013.01)

(58) Field of Classification Search
CPC .. C07D 235/12; C07D 263/57; C07D 277/66; A61P 35/00; A23L 33/10; A23L 33/30
See application file for complete search history.

(56) References Cited

U.S. PATENT DOCUMENTS

| | | | | |
|---|---|---|---|---|
| 8,673,911 | B2 * | 3/2014 | Mallais | C07D 277/30 548/200 |
| 9,125,901 | B2 | 9/2015 | Wang et al. | |
| 2006/0058553 | A1 * | 3/2006 | Leahy | C07D 207/16 562/622 |
| 2010/0305096 | A1 | 12/2010 | Castanedo et al. | |

FOREIGN PATENT DOCUMENTS

| | | |
|---|---|---|
| JP | 2010-195774 A | 9/2010 |
| KR | 10-2013-0026364 A | 3/2013 |
| WO | 03-066579 A2 | 8/2003 |
| WO | 2003/66579 * | 8/2003 |
| WO | 2006-017214 A2 | 2/2006 |
| WO | 2009-055917 A1 | 5/2009 |
| WO | 2010-087319 A1 | 8/2010 |
| WO | 2011-114202 A | 9/2011 |

OTHER PUBLICATIONS

International Search Report for PCT/KR2019/010443 mailed Dec. 2, 2019 from Korean Intellectual Property Office.
Chacko, S et al., "Expanding Benzoxazole-Based Inosine 5'-Monophosphate Dehydrogenase (IMPDH) Inhibitor Structure—Activity as Potential Antituberculosis Agents", Journal of Medical Chemistry, 2018, vol. 61, No. 11, pp. 4739-4756.

* cited by examiner

*Primary Examiner* — D Margaret M Seaman
(74) *Attorney, Agent, or Firm* — Revolution IP, PLLC

(57) ABSTRACT

A novel benzoheterocycle compound or a pharmaceutically acceptable salt thereof showed a high anti-proliferative effect against cancer cell lines. Using this, a pharmaceutical composition for preventing or treating cancer disease can comprise the compound or a pharmaceutically acceptable salt thereof as an active ingredient. In addition, a health functional food composition for preventing or improving cancer disease can include the compound or a pharmaceutically acceptable salt thereof as an active ingredient. The pharmaceutical composition or health functional food composition can effectively prevent or treat various cancer diseases.

6 Claims, 1 Drawing Sheet

[FIG. 1]
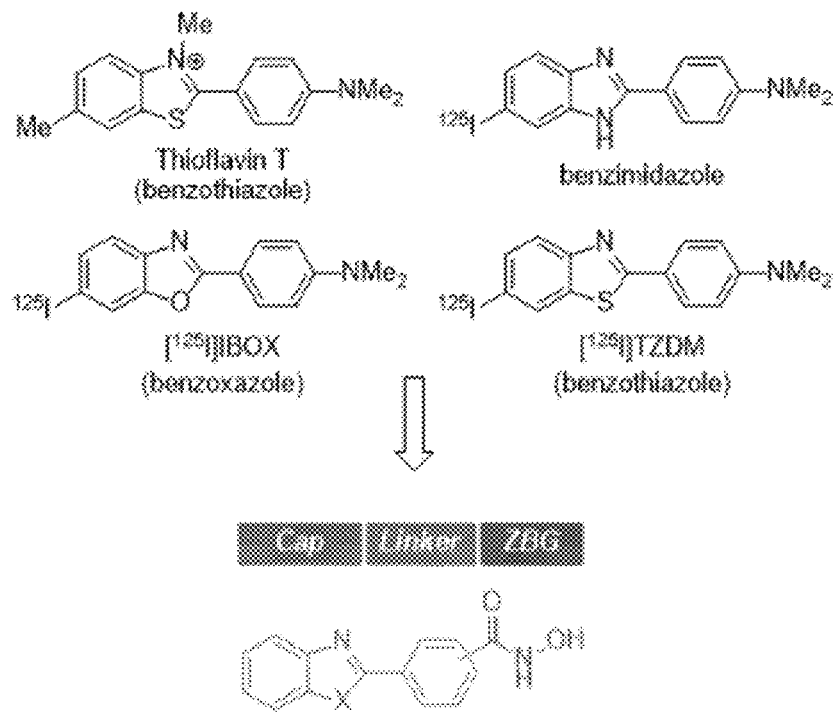
[FIG. 2]
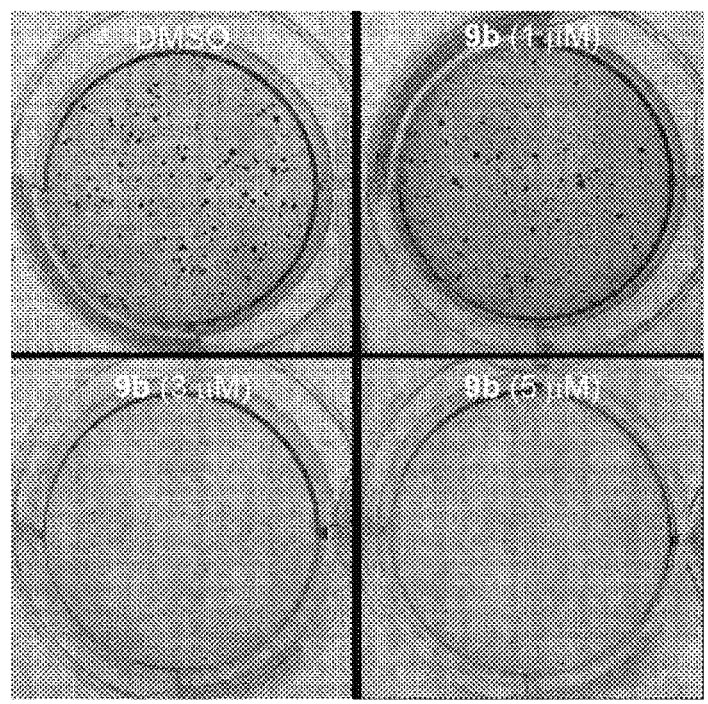

BENZO-HETEROCYCLIC COMPOUND AND COMPOSITION FOR PREVENTING OR TREATING CANCER DISEASE, CONTAINING SAME AS ACTIVE INGREDIENT

CROSS REFERENCE TO PRIOR APPLICATIONS

This application is the 35 U.S.C. 371 national stage of International application PCT/KR2019/010443 filed on Aug. 16, 2019; which claims priority to Korean Patent Application No. 10-2018-0130668 filed on Oct. 30, 2018. The entire contents of each of the above-identified applications are hereby incorporated by reference.

TECHNICAL FIELD

The present invention relates to a benzoheterocycle compound and a composition for preventing or treating cancer disease comprising the same as an active ingredient.

BACKGROUND ART

Brain tumor refers to any tumor that occurs in the skull and includes all tumors that occur in the brain and structures around the brain. Depending on the anatomical specificity of the brain, tumors in which cancer cells are not found, so-called benign tumors, are formed in the brain, and if the size is large, life may be lost due to an elevation in brain pressure.

One of them, brain cancer, which is a malignant brain tumor, is a cancer that causes great damage to the brain and has a very low survival rate. Primary brain cancer does not metastasize to other body organs, but metastatic brain cancer is caused by metastasis of lung cancer, breast cancer, and digestive system cancer to the brain. Primary brain cancer includes neuroma, astrocytoma, neuroblastoma, glioma, meningioma, oligodendroglioma, medulloblastoma, spinal cord tumor and neurilemmoma, but it is not limited thereto. Clinical symptoms of brain cancer include headache, epileptic seizures, vomiting, motor paralysis, overlapping objects, decreased vision, hormonal abnormalities, hearing loss, dizziness, and speech impairment.

As the conventional treatment for brain cancer, extraction by surgical operation is the most effective, depending on the type of brain cancer or the site of occurrence, surgery is often impossible, and the risk of postoperative complications is very high when completely excised. In addition, because there is a brain-blood barrier (BBB) that inhibits the penetration of drugs into the brain, the absorption of drugs is low, so in order to treat brain cancer with chemotherapy using anticancer drugs, it is necessary to administer a high concentration of anticancer drugs compared to other cancers. As a result, there is a problem that causes serious side effects to other organs of the body.

DISCLOSURE

Technical Problem

In order to solve the above problems, the present invention provides a novel compound or a pharmaceutically acceptable salt thereof.

The present invention provides a pharmaceutical composition for preventing or treating cancer diseases comprising a novel compound or a pharmaceutically acceptable salt thereof as an active ingredient.

In addition, the present invention provides a health functional food composition for preventing or improving cancer diseases comprising a novel compound or a pharmaceutically acceptable salt thereof as an active ingredient.

Technical Solution

The novel compound according to the present invention may be a compound represented by the following Chemical Formula 1 or a pharmaceutically acceptable salt thereof.

[Chemical Formula 1]

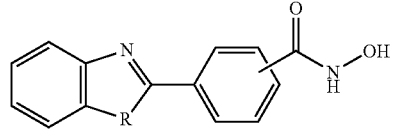

In Chemical Formula 1, R is selected from O, S, or $NR^1$ and $R^1$ may be selected from hydrogen, C1-C10 alkyl, C1-C4 alkoxy, halogen or nitro.

The pharmaceutical composition according to the present invention may comprise the compound represented by Chemical Formula 1 or a pharmaceutically acceptable salt thereof as an active ingredient.

The health functional food composition according to the present invention may comprise the compound represented by Chemical Formula 1 or a pharmaceutically acceptable salt thereof as an active ingredient.

Advantageous Effects

The novel compound or a pharmaceutically acceptable salt thereof according to the present invention has high anti-proliferative activity against cancer cell lines, and can be used as an effective anti-cancer therapeutic agent. The pharmaceutical composition for preventing or treating cancer diseases and a health functional food composition comprising the compound or a pharmaceutically acceptable salt thereof as an active ingredient can prevent, treat or improve various cancer diseases such as breast cancer and lung cancer as well as brain cancer.

DESCRIPTION OF DRAWINGS

FIG. 1 is a schematic design diagram of a novel compound derived from the structure of an amyloid-β probe.

FIG. 2 shows the inhibitory effect of Compound 9b according to an experimental example of the present invention.

BEST MODE

Hereinafter, the present invention will be described in detail.

FIG. 1 is a schematic design diagram of a novel compound derived from the structure of an amyloid-β probe. Substantial efforts have been undertaken to develop amyloid-β probes with high brain uptake, resulting in a variety of radiolabeled molecular probes for in vivo amyloid-β imaging. Among the scaffolds derived from the molecular probes, thioflavin-T analogues such as benzothiazole, benzoxazole and benzimidazole display not only excellent binding affinity to amyloid-β aggregates but also high uptake into the brain. Such benzoheterocycle is attracting attention in oncology due to various physiological activities in cancer treatment, and based on this, benzoheterocycle derivatives for the development of an anticancer agent having high central nervous system permeability were synthesized to complete the present invention.

The present invention provides a compound represented by the following Chemical Formula 1 or a pharmaceutically acceptable salt thereof:

[Chemical Formula 1]

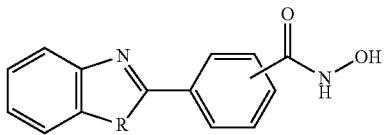

In Chemical Formula 1, R is selected from O, S or $NR^1$ and $R^1$ may be selected from hydrogen, C1-C10 alkyl, C1-C4 alkoxy, halogen or nitro.

Preferably, Chemical Formula 1, R is selected from O, S or $NR^1$ and $R^1$ may be hydrogen or C1-C4 alkyl, and more preferably, R may be O or S.

More specifically, the compound may be selected from the group consisting of 4-(1H-benzo[d]imidazol-2-yl)-N-hydroxybenzamide, N-hydroxy-4-(1-methyl-1H-benzo[d]imidazole-2-yl)benzamide, 4-(1-ethyl-1H-benzo[d]imidazol-2-yl)-N-hydroxybenzamide, N-hydroxy-4-(1-propyl-1H-benzo[d]imidazol-2-yl)benzamide, 4-(1-butyl-1H-benzo[d]imidazol-2-yl)-N-hydroxybenzamide, 4-(benzo[d]oxazole-2-yl)-N-hydroxybenzamide, 4-(benzo[d]thiazol-2-yl)-N-hydroxybenzamide, 3-(1H-benzo[d]amidazol-2-yl)-N-hydroxybenzamide, N-hydroxy-3-(1-methyl-1H-benzo[d]imidazol-2-yl)benzamide, 3-(1-ethyl-1H-benzo[d]imidazole-2-yl)-N-hydroxybenzamide, N-hydroxy-3-(1-propyl-1H-benzo[d]imidazol-2-yl)benzamide, 3-(1-butyl-1H-benzo[d]imidazol-2-yl)-N-hydroxybenzamide, 3-(benzo[d]oxazol-2-yl)-N-hydroxybenzamide and 3-(benzo[d]thiazol-2-yl)-N-hydroxybenzamide.

The compound according to the present invention may be used in the form of a pharmaceutically acceptable salt, and the salt may be used in the form of either a pharmaceutically acceptable basic salt or an acidic salt.

The basic salt can be used in the form of either an organic base salt or an inorganic base salt, and it may be selected from the group consisting of sodium salt, potassium salt, calcium salt, lithium salt, magnesium salt, cesium salt, aminium salt, ammonium salt, triethyl salt an aluminum salt and a pyridinium salt, but it is not limited thereto.

As acidic salts, acid addition salts formed by free acids are useful. Inorganic acids and organic acids can be used as the free acid, hydrochloric acid, bromic acid, sulfuric acid, sulfurous acid, phosphoric acid, double phosphoric acid, nitric acid, etc. can be used as inorganic acids, and citric acid, acetic acid, maleic acid, malic acid, fumaric acid, glucoic acid, methanesulfonic acid, benzenesulfonic acid, camphorsulfonic acid, oxalic acid, malonic acid, glutaric acid, acetic acid, glycolic acid, succinic acid, tartaric acid, 4-toluenesulfonic acid, galacturonic acid, embonic acid, glutamic acid, citric acid, aspartic acid, stearic acid, and the like can be used as organic acids. Preferably, hydrochloric acid may be used as the inorganic acid and methanesulfonic acid may be used as the organic acid.

In addition, the compound according to the present invention may include all salts, hydrates and solvates that can be prepared by conventional methods, as well as pharmaceutically acceptable salts. In the compound according to the present invention, the addition salt can be prepared by a conventional method and the addition salt can be prepared by dissolving the compound in a water-miscible organic solvent such as acetone, methanol, ethanol or acetonitrile and adding an excessive amount of organic base or an aqueous base solution of an inorganic base, followed by precipitation or crystallization. Alternatively, the mixture may be prepared by evaporating a solvent or an excess base and drying to obtain an addition salt, or by suction filtration of the precipitated salt. Alternatively, it may be prepared by evaporating solvent or excess base from the mixture and dry to obtain an addition salt, or suction-filtering the precipitated salt.

As used herein, "prevention" refers to any action of inhibiting or delaying the onset of a cancer disease or at least one symptom thereof by administrating the pharmaceutical composition or health functional food composition according to the present invention. In addition, it includes treatment of a subject with remission of the disease for the prophylaxis and the prevention of recurrence.

As used herein, "treatment" refers to any action that improves or beneficially alters the condition, such as alleviating, reducing or eliminating the onset of a cancer disease or at least one symptom thereof by administrating the pharmaceutical composition according to the present invention.

As used herein, "improvement" refers to any action of that improves or beneficially alters the condition, such as alleviating, reducing or eliminating the onset of a cancer disease or at least one symptom thereof by ingestion of the health functional food composition according to the present invention.

As used herein, "pharmaceutical composition" means a composition administered for a specific purpose, and for the purposes of the present invention, it refers to be administered to prevent or treat a cancer disease or at least one symptom thereof.

As used herein, "health functional food" has a meaning similar to food for specified health use (FoSHU), and refers to foods with high medical and medicinal effects processed so that the biological regulation function is effectively shown in addition to nutritional supply.

The present invention provides a pharmaceutical composition for preventing or treating cancer disease comprising the compound or a pharmaceutically acceptable salt thereof as an active ingredient.

In the pharmaceutical composition according to the present invention, since the compound or salt has anti-proliferative activity against cancer cells, it can be applied to various cancer diseases. The cancer disease may be selected from the group consisting of brain cancer, breast cancer, lung cancer, skin cancer, ovarian cancer, uterine cancer, prostate cancer, kidney cancer, colon cancer, pancreatic cancer, gastric cancer, liver cancer, colon cancer, head or neck cancer, laryngeal cancer, esophageal cancer, blood cancer and leukemia, but it is not limited thereto.

The pharmaceutical composition according to the present invention may be prepared by further comprising a suitable pharmaceutically acceptable carrier, excipient or diluent according to the above formulation. The "pharmaceutically acceptable" means exhibiting a property that is not toxic to cells or humans exposed to the pharmaceutical composition.

Carriers, excipients or diluents that can be used in the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate or mineral oil, but it is not limited thereto and any suitable agent known in the art may be used.

The pharmaceutical compositions of the present invention can be formulated and used in the form of oral formulations such as powders, granules, tablets, capsules, suspensions, emulsions, syrups, aerosols, external preparations, suppositories, or sterile injectable solutions according to a conventional method.

When the pharmaceutical composition according to the present invention is formulated in the above form, it may be prepared using diluents or excipients such as fillers, weighting agents, binders, wetting agents, disintegrants and surfactants that are commonly used. Solid preparations for oral administration include tablets, pills, powders, granules, capsules, and the like, and such a solid preparation may be prepared by mixing at least one excipient, for example, starch, calcium carbonate, sucrose, lactose, gelatin, etc.

Further, in addition to simple excipients, lubricants such as magnesium stearate and talc may also be used. It can be prepared by adding various excipients such as wetting agents, sweetening agents, fragrances, preservatives, and the like, in addition to liquids and liquid paraffins for oral use.

Formulations for parenteral administration include sterile aqueous solutions, non-aqueous solvents, suspensions, emulsions, lyophilized formulations, and suppositories. As the non-aqueous solvent and suspending agent, propylene glycol, polyethylene glycol, vegetable oil such as olive oil, injectable ester such as ethyl oleate, and the like may be used. As a base for suppositories, witepsol, macrosol, Tween 61, cacao butter, laurin, glycerogelatin, and the like may be used.

In addition, calcium or vitamin $D_3$ may be added to enhance therapeutic efficacy.

In the pharmaceutical composition according to the present invention, the pharmaceutical composition may be administered in a pharmaceutically effective amount. The "pharmaceutically effective amount" means an amount sufficient to treat a disease at a reasonable benefit/risk ratio applicable to medical treatment and not causing side effects, and effective dosage levels can be determined according to factors including the patient's health status, type of ulcer, severity, activity of the drug, sensitivity to the drug, administration method, administration time, administration route and rate of excretion, duration of treatment, drugs used in combination or concurrently, and other factors well known in the medical field.

The amount of the compound, which is an active ingredient in the pharmaceutical composition according to the present invention, may vary depending on the patient's age, sex, weight, and disease, but 0.001 to 100 mg/kg, preferably 0.01 to 10 mg/kg may be administered once to several times a day. In addition, the dosage of the compound according to the present invention may be increased or decreased depending on the route of administration, the degree of disease, sex, weight, age and the like. Therefore, the above dosage does not limit the scope of the present invention in any way.

The pharmaceutical composition may be administered to mammals such as mice, mice, livestock, and humans by various routes. All modes of administration can be expected, for example, it can be administered by oral, rectal or intravenous, intramuscular, subcutaneous, intrabronchial inhalation, Intrauterine septum or intracere-broventricular injection.

In addition, the present invention provides a health functional food composition for preventing or improving cancer disease comprising the compound or a pharmaceutically acceptable salt thereof as an active ingredient.

In the health functional food composition according to the present invention, since the compound or salt has antiproliferative activity against cancer cells, it can be applied to various cancer diseases. The cancer disease may be selected from the group consisting of brain cancer, breast cancer, lung cancer, skin cancer, ovarian cancer, uterine cancer, prostate cancer, kidney cancer, colon cancer, pancreatic cancer, gastric cancer, liver cancer, colon cancer, head or neck cancer, laryngeal cancer, esophageal cancer, blood cancer and leukemia, but it is not limited thereto.

The health functional food according to the present invention may be provided in the form of powder, granule, tablet, capsule, syrup or beverage, and the health functional food is used with other foods or food additives in addition to the compound according to the present invention, which is an active ingredient and it can be suitably used according to a conventional method. The mixing amount of the active ingredient may be appropriately determined according to the purpose of its use, for example, prevention, health or therapeutic treatment.

The effective dose of the compound contained in the health functional food according to the present invention can be used in accordance with the effective dose of the pharmaceutical composition, but in the case of long-term intake for the purpose of health and hygiene or for health control purposes, it may be the above range or less, and since there is no problem in terms of safety, the active ingredient may be used in an amount of at least the above range.

There is no particular limitation on the type of health functional food according to the present invention, and examples include meat, sausage, bread, chocolate, candy, snacks, confectionery, pizza, ramen, other noodles, gum, dairy products including ice cream, various soups, beverages, teas, drinks, alcoholic beverages, vitamin complexes and the like.

Hereinafter, the present invention will be described in more detail through examples. These examples are only intended to illustrate the present invention in more detail, and it will be apparent to those skilled in the art that the scope of the present invention is not limited by these examples according to the gist of the present invention. The examples of the present invention are provided to more completely explain the present invention to those of ordinary skill in the art.

Preparation for Synthesis

All reagents and solvents were purchased from commercial suppliers and used without further purification. All experiments dealing with moisture-sensitive compounds were carried out under argon atmosphere. Concentration or solvent removal under reduced pressure was performed using a rotary evaporator. Analytical thin layer chromatography was performed on precoated silica gel $F_{254}$ TLC plates (E, Merck) with visualization under UV light or by staining using iodine gas. Column chromatography was conducted under medium pressure on silica (Merck Silica Gel 40-63m) or performed by using a Biotage SP1 flash purification system with a prepacked silica gel cartridge (Biotage). NMR analysis was performed using JNM-ECZ500R (500 MHZ) manufactured by Jeol resonance.

Chemical shifts (δ) were reported in parts per million. The deuterium lock signal of the sample solvent was used as a reference, and the coupling constants (J) were expressed in Hertz (Hz). The splitting pattern abbreviations are as follows: s, singlelet; d, doublet; t, triplet; q, quartert; dd, doublet of doublets; td, triplet of doublet; m, multiplet.

The purity of all final compounds was confirmed to be higher than 95% by analytical HPLC performed with a dual pump Shimadzu LC-6AD system equipped with a VP-ODS C18 column.

[Example 1] Compound Synthesis (5, 6a-d)

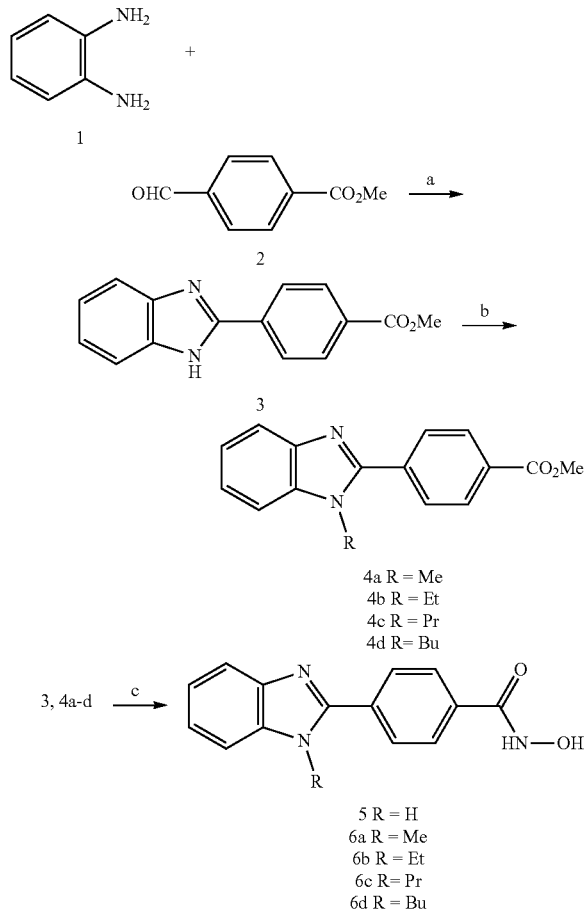

[Reaction Scheme 1]

The above Reaction Scheme 1 shows the synthesis process of Compound 5 and Compound 6a-6d.

Referring to Scheme 1, briefly, reaction of ortho-phenylenediamine 1 with aldehyde 2 in aqueous dimethylformamide (hereinafter, DMF) provided a key intermediate, compound 3 via aerobic oxidation in 88% yield. Compound 3 was treated with sodium hydride in DMF for 2 hours, followed by the addition of various alkyl iodides to provide Compounds 4a-4d in yields of 45-70%. Finally, Compounds 3 and 4a-4d were sequentially treated with $NH_2OH$ and KOH in methanol to obtain Compounds 5 and 6a-6d in yields of 32-35%. In more detail, the process was performed as follows.

(1-1) Compound 3: Methyl 4-(1H-benzo[d]imidazol-2-yl)benzoate

A mixture of o-phenylenediamine (5.84 g, 53.98 mmol) and methyl 4-formylbenzoate (9.75 mL, 59.37 mmol) in 180 mL of DMF and 20 mL of water was stirred at 80° C. for 36 hours under open flask. The mixture was concentrated under reduced pressure and purified by a column to afford Compound 3 in a yield of 88%. $R_f$=0.23 (3:7=ethyl acetate:hexane).

$^1$H NMR (500 MHz, $CD_3OD$) δ 8.19-8.14 (m, 4H), 7.63 (s, 2H), 7.30-7.27 (m, 2H), 3.93 (s, 3H). $^{13}$C NMR (125 MHz, $CD_3OD$) δ 166.5, 150.6, 133.9, 131.2, 129.9, 126.4, 123.1, 51.5.

(1-2) Compound 4a: Methyl 4-(1-methyl-1H-benzo[d]imidazol-2-yl)benzoate

60% sodium hydride (0.09 g, 3.75 mmol) in DMF (5 mL) was added to Compound 3 (0.32 g, 1.25 mmol) in DMF (5 mL) at 0° C. The mixture was stirred at room temperature for 2 hours. Iodomethane (0.09 mL, 1.38 mmol) was added and stirred for 8 hours. The reaction was diluted with ethyl acetate. The organic layer was washed with water, dried over $Na_2SO_4$, concentrated under reduced pressure and purified by MPLC to afford Compound 4a in 70% yield. $R_f$=0.26 (3:7=ethyl acetate:hexane).

$^1$H NMR (500 MHz, $CDCl_3$) δ 8.17 (d, J=8.5 Hz, 2H), 7.85-7.81 (m, 3H), 7.38-7.36 (m, 1H), 7.33-7.30 (m, 2H), 3.94 (s, 3H), 3.84 (s, 3H). $^{13}$C NMR (125 MHz, $CDCl_3$) δ 166.5, 152.5, 143.0, 136.7, 134.5, 131.1, 129.9, 129.4, 123.3, 122.7, 120.1, 109.8, 52.4, 31.8.

(1-3) Compound 4b: Methyl 4-(1-ethyl-1H-benzo[d]imidazol-2-yl)benzoate

60% sodium hydride (0.09 g, 3.75 mmol) in DMF (5 mL) was added to Compound 3 (0.32 g, 1.25 mmol) in DMF (5 mL) at 0° C. The mixture was stirred at room temperature for 2 hours. Iodoethane (0.09 mL, 1.38 mmol) was added and stirred for 8 hours. The reaction was diluted with ethyl acetate. The organic layer was washed with water, dried over $Na_2SO_4$, concentrated under reduced pressure and purified by MPLC to obtain Compound 4b in a yield of 49%. $R_f$=0.25 (3:7=ethyl acetate:hexane).

$^1$H NMR (500 MHz, $CDCl_3$) δ 8.19 (d, J=8.5 Hz, 2H), 7.85-7.81 (m, 3H), 7.45-7.43 (m, 1H), 7.35-7.31 (m, 2H), 4.32-4.27 (m, 2H), 3.96 (s, 3H), 1.47 (t, J=7.0 Hz, 3H). $^{13}$C NMR (125 MHz, $CDCl_3$) δ 166.6, 152.3, 143.3, 135.6, 134.9, 131.2, 130.0, 129.3, 123.2, 122.7, 120.3, 110.1, 52.4, 39.8, 15.4. ESI MS (m/e) 181.12 $[M+H]^+$.

(1-4) Compound 4c: Methyl 4-(1-propyl-1H-benzo[d]imidazol-2-yl)benzoate

60% sodium hydride (0.08 g, 3.50 mmol) in DMF (5 mL) was added to Compound 3 (0.32 g, 1.25 mmol) in DMF (5 mL) at 0° C. The mixture was stirred at room temperature for 2 hours. Iodopropane (0.13 mL, 1.28 mmol) was added and stirred for 8 hours. The reaction was diluted with ethyl acetate. The organic layer was washed with water, dried over $Na_2SO_4$, concentrated under reduced pressure and purified by MPLC to obtain Compound 4c in a yield of 45%. $R_f$=0.30 (3:7=ethyl acetate:hexane).

$^1$H NMR (500 MHz, $CDCl_3$) δ 8.19 (d, J=8.5 Hz, 2H), 7.83-7.79 (m, 3H), 7.42-7.40 (m, 1H), 7.33-7.29 (m, 2H), 4.19 (t, J=7.5 Hz, 2H), 3.95 (s, 3H), 1.85-1.80 (m, 2H), 0.84

(t, J=7.1 Hz, 3H). $^{13}$C NMR (125 MHz, CDCl$_3$) δ 166.5, 152.5, 143.0, 136.7, 134.5, 131.1, 129.9, 129.4, 123.3, 122.7, 120.1, 109.8, 52.4, 31.8, 29.7, 15.4. ESI MS (m/e) 195.14 [M+H]$^+$.

(1-5) Compound 4d: Methyl 4-(1-butyl-1H-benzo[d]imidazol-2-yl)benzoate

60% sodium hydride (0.09 g, 3.60 mmol) in DMF (5 mL) was added to Compound 3 (0.30 g, 1.20 mmol) in DMF (5 mL) at 0° C. The mixture was stirred at room temperature for 2 hours. Iodobutane (0.15 mL, 1.32 mmol) was added and stirred for 8 hours. The reaction was diluted with ethyl acetate. The organic layer was washed with water, dried over Na$_2$SO$_4$, concentrated under reduced pressure and purified by MPLC to obtain Compound 4d in a yield of 46%. R$_f$=0.35 (3:7=ethyl acetate:hexane).

$^1$H NMR (500 MHz, CDCl$_3$) δ 8.17 (d, J=8.5 Hz, 2H), 7.85-7.81 (m, 3H), 7.38-7.36 (m, 1H), 7.33-7.30 (m, 2H), 4.20 (t, J=7.5 Hz, 2H), 3.94 (s, 3H), 1.81-1.74 (m, 2H), 1.24-1.22 (m, 2H), 0.83 (t, J=7.5 Hz, 3H). $^{13}$C NMR (125 MHz, CDCl$_3$) δ 166.5, 152.5, 143.0, 136.7, 134.5, 131.1, 129.9, 129.4, 123.3, 122.7, 120.1, 109.8, 52.4, 44.6, 31.9, 19.9, 13.5.

(1-6) Compound 5: 4-(1H-benzo[d]imidazol-2-yl)-N-hydroxybenzamide

Hydroxylamine hydrochloride (3.72 g, 53.51 mmol) in methanol (5 mL) was added to a solution of potassium hydroxide (3.00 g, 53.51 mmol) in methanol (5 mL) at 0° C. The mixture was stirred at 0° C. for 15 minutes, and the precipitated potassium chloride was removed and the filtrate was used as such, To a solution of Compound 3 (0.30 g, 1.19 mmol) in tetrahydrofuran (10 mL) was added to freshly prepared hydroxylamine at 0° C. and stirred at the same temperature for 2 hours. The mixture was neutralized to pH 7 with acetic acid and extracted with ethyl acetate. The organic layer was dried over Na$_2$SO$_4$, concentrated under reduced pressure, and purified by MPLC to obtain Compound 5 in a yield of 40%. R$_f$=0.08 (9:1=ethyl acetate:hexane).

$^1$H NMR (500 MHz, DMSO-D$_6$) δ 8.13 (d, J=8.5 Hz, 2H), 7.89 (d, J=8.0 Hz, 2H), 7.59-7.57 (m, 2H), 7.20-7.18 (m, 2H). $^{13}$C NMR (125 MHz, DMSO-D$_6$) δ 163.3, 151.2, 137.2, 130.4, 126.6, 125.9, 122.1. ESI MS (m/e) 254.09 [M+H]$^+$.

(1-7) Compound 6a: N-hydroxy-4-(1-methyl-1H-benzo[d]imidazol-2-yl)benzamide

Hydroxylamine hydrochloride (1.29 g, 18.6 mmol) in methanol (5 mL) was added to a solution of potassium hydroxide (1.04 g, 18.6 mmol) in methanol (5 mL) at 0° C. The mixture was stirred at 0° C. for 15 minutes, and the precipitated potassium chloride was removed and the filtrate was used as such; To a solution of Compound 4a (0.11 g, 0.41 mmol) in tetrahydrofuran (10 mL) at 0° C. was added to freshly prepared hydroxylamine and stirred at the same temperature for 2 hours. The mixture was neutralized to pH 7 with 3N HCl and extracted with ethyl acetate. The organic layer was dried over Na$_2$SO$_4$, concentrated under reduced pressure, and purified by MPLC to obtain Compound 6a in a yield of 36%. R$_f$=0.17 (9:1=ethyl acetate:hexane).

$^1$H NMR (500 MHz, DMSO-D$_6$) δ 8.11 (d, J=8.0 Hz, 2H), 8.02 (d, J=8.5 Hz, 1H), 7.91 (dd, J=8.0 Hz, 1.5 Hz, 1H), 7.86 (d, J=8.5 Hz, 1H), 7.69 (t, J=8.5 Hz, 1H), 7.62 (d, J=8.0 Hz, 1H), 7.43 (t, J=7.5 Hz, 1H), 3.71 (s, 3H). $^{13}$C NMR (125 MHz, DMSO-D$_6$) δ 154.5, 152.9, 138.8, 134.5, 133.9, 132.8, 131.5, 130.3, 129.8, 129.7, 129.2, 126.7, 124.3, 115.4, 29.8. ESI MS (m/e) 167.11 [M+H]$^+$.

(1-8) Compound 6b: 4-(1-ethyl-1H-benzo[d]imidazol-2-yl)-N-hydroxybenzamide

Hydroxylamine hydrochloride (1.12 g, 16.05 mmol) in methanol (5 mL) was added to a solution of potassium hydroxide (0.90 g, 16.05 mmol) in methanol (5 mL) at 0° C. The mixture was stirred at 0° C. for 15 minutes and the precipitated potassium chloride was removed and the filtrate was used as such; To a solution of Compound 4b (0.10 g, 0.36 mmol) in tetrahydrofuran (10 mL) was added to freshly prepared hydroxylamine at 0° C. and stirred at the same temperature for 3 hours. The mixture was neutralized to pH 7 with acetic acid and extracted with ethyl acetate. The organic layer was dried over Na$_2$SO$_4$, concentrated under reduced pressure, and purified by MPLC to obtain Compound 6b in a yield of 51%. R$_f$=0.19 (9:1=ethyl acetate:hexane).

$^1$H NMR (500 MHz, DMSO-D$_6$) δ 11.42 (s, 1H), 9.22 (s, 1H), 7.95 (d, J=7.5 Hz, 2H), 7.87 (d, J=8.5 Hz, 2H), 7.71 (d, J=8.0 Hz, 1H), 7.67 (d, J=8.0 Hz, 1H), 7.33-7.25 (m, 2H), 4.34 (q, J=7.5 Hz, 2H), 1.33 (t, J=7.5 Hz, 3H). $^{13}$C NMR (125 MHz, CD$_3$OD) δ 167.1, 153.6, 143.4, 136.4, 135.2, 134.2, 130.7, 128.7, 124.6, 124.1, 119.9, 111.9, 40.8, 15.4. ESI MS (m/e) 282.12 [M+H]$^+$.

(1-9) Compound 6c: N-hydroxy-4-(1-propyl-1H-benzo[d]imidazol-2-yl)benzamide

Hydroxylamine hydrochloride (1.06 g, 15.29 mmol) in methanol (5 mL) was added to a solution of potassium hydroxide (0.86 g, 15.29 mmol) in methanol (5 mL) at 0° C. The mixture was stirred at 0° C. for 15 minutes and the precipitated potassium chloride was removed and the filtrate was used as such, To a solution of compound 4c (0.11 g, 0.34 mmol) in tetrahydrofuran (10 mL) was added to freshly prepared hydroxylamine at 0° C. and stirred at the same temperature for 2 hours. The mixture was neutralized to pH 7 with acetic acid and extracted with ethyl acetate. The organic layer was dried over Na$_2$SO$_4$, concentrated under reduced pressure and purified by MPLC to obtain Compound 6c in a yield of 49%. R$_f$=0.19 (9:1=ethyl acetate:hexane).

$^1$H NMR (500 MHz, DMSO-D$_6$) δ 11.41 (s, 1H), 9.19 (s, 1H), 7.93 (d, J=8.5 Hz, 2H), 7.86 (d, J=8.5 Hz, 2H), 7.70 (d, J=8.5 Hz, 2H), 7.33-7.25 (m, 2H), 4.29 (t, J=7.5 Hz, 2H), 1.72-1.65 (m, 2H), 0.72 (t, J=7.5 Hz, 3H). $^{13}$C NMR (125 MHz, DMSO-D$_6$) δ 163.7, 152.1, 142.2, 135.7, 133.8, 132.9, 129.3, 127.4, 122.8, 122.3, 119.2, 111.2, 45.7, 22.7, 11.0. ESI MS (m/e) 296.14 [M+H]$^+$.

(1-10) Compound 6d: 4-(1-butyl-1H-benzo[d]imidazol-2-yl)-N-hydroxybenzamide

Hydroxylamine hydrochloride (2.03 g, 29.19 mmol) in methanol (5 mL) was added to a solution of potassium hydroxide (1.64 g, 29.19 mmol) in methanol (5 mL) at 0° C. The mixture was stirred at 0° C. for 15 minutes and the precipitated potassium chloride was removed and the filtrate was used as such, To a solution of compound 4d (0.20 g, 0.65 mmol) in tetrahydrofuran (10 mL) was added to freshly prepared hydroxylamine at 0° C. and stirred at the same temperature for 3 hours. The mixture was neutralized to pH 7 with acetic acid and extracted with ethyl acetate. The organic layer was dried over Na$_2$SO$_4$, concentrated under reduced pressure and purified by MPLC to obtain Compound 6d in a yield of 51%. R$_f$=0.26 (9:1=ethyl acetate: hexane).

$^1$H NMR (500 MHz, DMSO-D$_6$) δ 11.40 (s, 1H), 9.18 (s, 1H), 7.93 (d, J=8.5 Hz, 2H), 7.86 (d, J=8.0 Hz, 2H), 7.68 (t, J=8.5 Hz, 2H), 7.32-7.24 (m, 2H), 4.32 (t, J=7.0 Hz, 2H), 1.67-1.61 (m, 2H), 1.16-1.08 (m, 2H), 0.74 (t, J=7.5 Hz, 3H). $^{13}$C NMR (125 MHz, DMSO-D$_6$) δ 164.1, 152.6, 143.1, 136.2, 134.1, 133.6, 129.7, 127.8, 123.2, 122.6, 119.8, 111.6, 44.4, 31.7, 19.7, 13.8. ESI MS (m/e) 310.16 [M+H]$^+$.

[Example 2] Compound Synthesis (9a-b)

[Reaction Scheme 2]

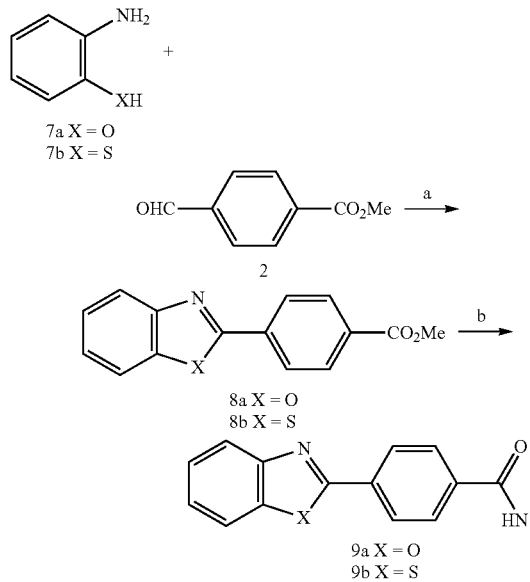

Reaction Scheme 2 shows the synthesis process for Compounds 9a-9b.

Referring to Reaction Scheme 2, Compounds 8a and 8b were synthesized by iodine-mediated cyclization of 2-aminophenol 7a or 2-aminothiophenol 7b, which are the corresponding starting materials, together with aldehyde 2 in yields of 32-35%. Compounds 9a and 9b were successfully obtained in yields of 42-45% by sequentially treating esters 8a and 8b with NH$_2$OH and KOH in methanol. In more detail, the process was performed as follows.

(2-1) Compound 8a: Methyl 4-(benzo[d]oxazol-2-yl)benzoate

2-Aminophenol (0.20 g, 1.83 mmol) and methyl 4-formylbenzoate (0.30 g, 1.83 mmol) were dissolved in dichloromethane (20 ml), and stirred for 4 hours under an argon atmosphere at room temperature. The reaction mixture was added to iodine (0.12 g, 0.92 mmol) and stirred in an open flask at room temperature for 1 hour. The mixture was concentrated under reduced pressure and purified by a column to obtain Compound 8a in a yield of 32%. R$_f$=0.31 (1:9=ethyl acetate:hexane).

$^1$H NMR (500 MHz, CDCl$_3$) δ 8.32 (d, J=8.5 Hz, 2H), 8.18 (d, J=8.5 Hz, 2H), 7.80-7.79 (m, 1H), 7.61-7.59 (m, 1H), 7.40-7.37 (m, 2H), 3.96 (s, 3H). $^{13}$C NMR (125 MHz, CDCl$_3$) δ 166.5, 162.1, 151.0, 142.1, 132.6, 131.1, 130.2, 127.6, 125.9, 125.0, 120.5, 110.9, 52.6.

(2-2) Compound 8b: Methyl 4-(benzo[d]thiazol-2-yl)benzoate

2-Aminothiophenol (1.71 mL, 15.98 mmol) and methyl 4-formylbenzoate (2.62 g, 15.98 mmol) were dissolved in dichloromethane (100 mL), and stirred for 4 hours under an argon atmosphere at room temperature. The reaction mixture was added to iodine (1.01 g, 7.99 mmol) and stirred in an open flask at room temperature for 45 minutes. The mixture was concentrated under reduced pressure and purified by a column to obtain Compound 8b in a yield of 35%. R$_f$=0.31 (1:9=ethyl acetate:hexane).

$^1$H NMR (500 MHz, CDCl$_3$) δ 8.15-8.14 (m, 4H), 8.09 (d, J=7.5 Hz, 1H), 7.91 (d, J=8.5 Hz, 1H), 7.51 (t, J=8.0 Hz, 1H), 7.41 (t, J=7.5 Hz, 1H), 3.95 (s, 3H). $^{13}$C NMR (125 MHz, CDCl$_3$) δ 166.5, 154.2, 137.6, 135.4, 132.2, 130.4, 129.7, 127.6, 126.7, 125.8, 123.7, 121.9, 52.5.

(2-3) Compound 9a: 4-(benzo[d]oxazol-2-yl)-N-hydroxybenzamide

Hydroxylamine hydrochloride (2.47 g, 35.56 mmol) in methanol (5 mL) was added to a solution of potassium hydroxide (1.99 g, 35.56 mmol) in methanol (5 mL) at 0° C. The mixture was stirred at 0° C. for 15 minutes and the precipitated potassium chloride was removed and the filtrate was used as such, To a solution of Compound 8a (0.2 g, 0.79 mmol) in tetrahydrofuran (10 mL) was added to freshly prepared hydroxylamine at 0° C. and stirred at the same temperature for 2 hours. The mixture was neutralized to pH 7 with 3N HCl and extracted with ethyl acetate. The organic layer was dried over Na$_2$SO$_4$, concentrated under reduced pressure and purified by MPLC to obtain Compound 9a in a yield of 45%. R$_f$=0.24 (7:3=ethyl acetate:hexane).

$^1$H NMR (500 MHz, DMSO-D$_6$) δ 11.41 (s, 1H), 9.17 (s, 1H), 8.12 (d, J=8.0 Hz, 2H), 8.01 (d, J=8.5 Hz, 2H), 7.71 (d, J=8.0 Hz, 1H), 7.66 (d, J=8.0 Hz, 1H), 7.33 (t, J=6.5 Hz, 1H), 7.29 (t, J=7.5 Hz, 1H). $^{13}$C NMR (125 MHz, DMSO-Ds) δ 163.3, 161.5, 150.3, 141.4, 135.7, 128.6, 127.9, 127.3, 125.9, 125.1, 120.1, 111.1. ESI MS (m/e) 255.08 [M+H]$^+$.

(2-4) Compound 9b: 4-(benzo[d]thiazol-2-yl)-N-hydroxybenzamide

Hydroxylamine hydrochloride (43.44 g, 3.02 mmol) in methanol (5 mL) was added to a solution of potassium hydroxide (43.44 g, 2.24 mmol) in methanol (5 mL) at 0° C. The mixture was stirred at 0° C. for 15 minutes and the precipitated potassium chloride was removed and the filtrate was used as such; To a solution of compound 8b (0.26 g, 0.79 mmol) in tetrahydrofuran (10 mL) was added to freshly prepared hydroxylamine at 0° C. and stirred at the same temperature for 2 hours. The mixture was neutralized to pH 7 with 3N HCl and extracted with ethyl acetate. The organic layer was dried over Na$_2$SO$_4$, concentrated under reduced pressure and purified by MPLC to obtain Compound 9b in a yield of 42%. R$_f$=0.30 (7:3=ethyl acetate:hexane).

$^1$H NMR (500 MHz, DMSO-D$_6$) δ 11.41 (s, 1H), 9.19 (s, 1H), 8.19-8.17 (m, 3H), 8.10 (d, J=8.0 Hz, 1H), 7.94 (d, J=9.0 Hz, 2H), 7.57 (t, J=7.3 Hz, 1H), 7.49 (t, J=7.3 Hz, 1H). $^{13}$C NMR (125 MHz, DMSO-D$_6$) δ 166.4, 163.2, 153.5, 135.1, 135.0, 134.7, 127.9, 127.2, 126.9, 125.9, 123.1, 122.5. ESI MS (m/e) 271.05 [M+H]$^+$.

[Example 3] Compound Synthesis (13, 14a-d)

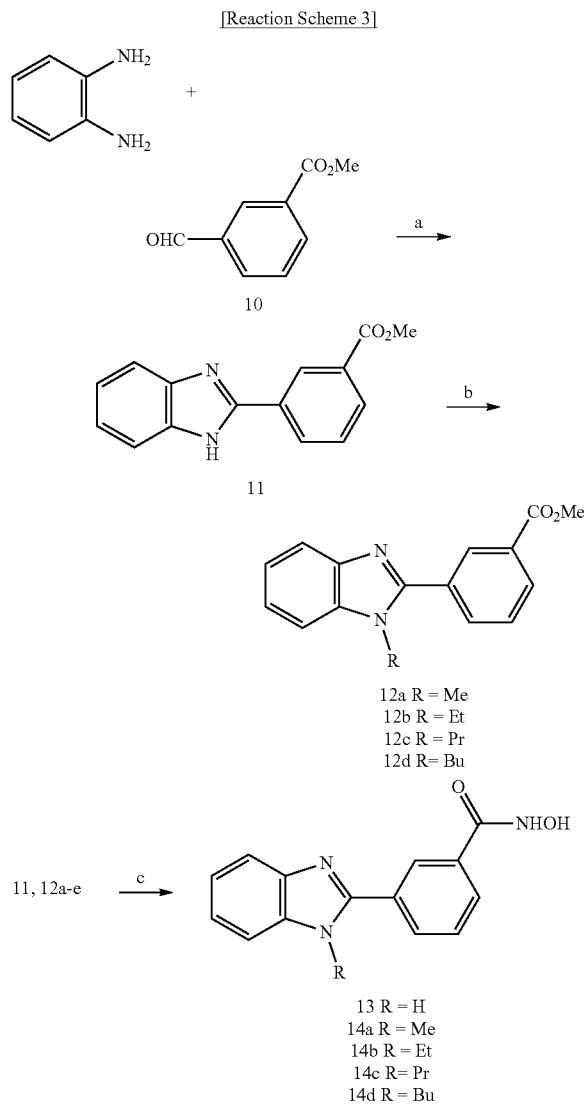

[Reaction Scheme 3]

Reaction Scheme 3 shows the synthesis process of Compounds 13 and 14a-14e in order to explore the biological activity of meta-regioisomers.

Referring to Reaction Scheme 3, similarly to Reaction Scheme 1, Compound 11 was obtained from ortho-phenylenediamine 1 with aldehyde 10 in aqueous DMF in a yield of 86%. Compound 11 was treated with sodium hydride in DMF for 2 hours and then alkylated with the corresponding alkyl iodides to obtain Compounds 12a-12d in yields of 11-91%. Compound 13 and Compounds 14a-14d was finally obtained in 33-55% yields through the reaction of Compound 11 and Compounds 12a-12d with NH$_2$OH and KOH in methanol.

(3-1) Compound 11: Methyl 3-(1H-benzo[d]imidazol-2-yl)benzoate

A mixture of o-phenylenediamine (2.00 g, 18.50 mmol) and methyl 3-formylbenzoate (3.03 g, 18.50 mmol) in 180 mL of DMF and 20 mL of water was stirred at 80° C. for 48 hours under open flask The mixture was concentrated under reduced pressure and purified by a column to obtain Compound 11 in a yield of 86%. $R_f$=0.25 (3:7=ethyl acetate:hexane).

$^1$H NMR (500 MHz, DMSO-d$_6$) δ 8.80 (s, 1H), 8.45 (d, J=8 Hz, 1H), 8.05 (d, J=7.5 Hz, 1H), 7.70 (t, J=8.0 Hz, 1H), 7.63 (s, 2H), 7.23-7.22 (m, 2H), 3.92 (s, 3H). $^{13}$C NMR (125 MHz, DMSO-D$_6$) 165.9, 150.3, 131.0, 130.8, 130.7, 130.5, 130.3, 129.6, 127.1, 127.1, 127.0, 122.6, 122.3, 52.4. ESI MS (m/e) 253.10 [M+H]$^+$.

(3-2) Compound 12a: Methyl 3-(1-methyl-1H-benzo[d]imidazol-2-yl)benzoate

60% sodium hydride (0.05 g, 1.24 mmol) in DMF (5 mL) was added to compound 11 (0.21 g, 0.82 mmol) in DMF (5 mL) at 0° C. The mixture was stirred at room temperature for 2 hours. Iodomethane (0.06 mL, 0.91 mmol) was added and stirred for 2.5 hours. The reaction was diluted with ethyl acetate. The organic layer was washed with water, dried over Na$_2$SO$_4$, concentrated under reduced pressure and purified by MPLC to obtain Compound 12a in a yield of 91%. $R_f$=0.25 (4:6=ethyl acetate:hexane).

$^1$H NMR (500 MHz, CDCl$_3$) δ 8.44 (s, 1H), 8.19 (d, J=8.0 Hz, 1H), 8.02 (d, J=7.5 Hz, 1H), 7.85-7.83 (m, 1H), 7.63 (t, J=8.0 Hz, 1H), 7.43-7.41 (m, 1H), 7.37-7.33 (m, 2H), 4.0 (s, 3H), 3.90 (s, 3H). $^{13}$C NMR (125 MHz, DMSO-D$_6$) δ 166.6, 152.8, 143.0, 134.0, 130.9, 130.8, 130.4, 129.2, 123.2, 122.8, 120.1, 109.9, 52.5, 31.97. ESI MS (m/e) 267.11 [M+H]$^+$.

(3-3) Compound 12b: Methyl 3-(1-ethyl-1H-benzo[d]imidazol-2-yl)benzoate

60% sodium hydride (0.05 g, 2.04 mmol) in DMF (5 mL) was added to compound 11 (0.20 g, 0.81 mmol) in DMF (5 mL) at 0° C. The mixture was stirred at room temperature for 2 hours. Iodoethane (0.07 mL, 0.89 mmol) was added and stirred for 2.5 hours. The reaction was diluted with ethyl acetate. The organic layer was washed with water, dried over Na$_2$SO$_4$, concentrated under reduced pressure and purified by MPLC to obtain Compound 12b in a yield of 11%. $R_f$=0.28 (4:6=ethyl acetate:hexane).

$^1$H NMR (500 MHz, CDCl$_3$) δ 8.41 (s, 1H), 8.19 (d, J=8.0 Hz, 1H), 7.97 (d, J=8.0 Hz, 1H), 7.84 (d, J=8.5 Hz, 1H), 7.63 (t, J=8.0 Hz, 1H), 7.45 (d, J=9.5 Hz, 1H), 7.36-7.26 (m, 2H), 4.31 (q, J=7.5 Hz, 2H), 3.96 (s, 3H), 1.50 (t, J=7.0 Hz, 3H). $^{13}$C NMR (125 MHz, DMSO-D$_6$) δ 166.6, 152.4, 143.3, 135.5, 133.9, 131.1, 131.9, 130.8, 130.3, 129.2, 123.1, 122.7, 120.3, 110.2, 52.5, 39.9, 15.4. ESI MS (m/e) 281.13 [M+H]$^+$.

(3-4) Compound 12c: Methyl 3-(1-propyl-1H-benzo[d]imidazol-2-yl)benzoate

60% sodium hydride (0.07 g, 1.78 mmol) in DMF (5 mL) was added to compound 11 (0.30 g, 1.19 mmol) in DMF (5 mL) at 0° C. The mixture was stirred at room temperature for 2 hours. Iodopropane (0.12 mL, 1.31 mmol) was added and stirred for 8 hours. The reaction was diluted with ethyl acetate. The organic layer was washed with water, dried over Na$_2$SO$_4$, concentrated under reduced pressure and purified by MPLC to obtain Compound 12c in a yield of 28%. $R_f$=0.32 (3:7=ethyl acetate:hexane).

$^1$H NMR (500 MHz, CDCl$_3$) δ 8.38 (t, J=1.0 Hz, 1H), 8.17 (td, J=8.0 Hz, 1.0 Hz, 1H), 7.94 (td, J=7.5 Hz, 2.0 Hz,

1H), 7.83-7.81 (m, 1H), 7.59 (t, J=8.0 Hz, 1H), 7.42-7.40 (m, 1H), 7.31-7.29 (m, 2H), 4.19 (t, J=7.5 Hz, 2H), 3.93 (s, 3H), 1.87-1.82 (m, 2H), 0.85 (t, J=7.0 Hz, 3H). $^{13}$C NMR (125 MHz, CDCl$_3$) δ 166.4, 152.6, 143.1, 135.7, 133.9, 131.1, 130.7, 130.2, 129.1, 123.0, 122.5, 120.1, 110.3, 52.4, 46.4, 23.3, 11.2. ESI MS (m/e) 295.14 [M+H]$^+$.

(3-5) Compound 12d: Methyl 3-(1-butyl-1H-benzo [d]imidazol-2-yl)benzoate

60% sodium hydride (0.07 g, 1.78 mmol) in DMF (5 mL) was added to compound 11 (0.30 g, 1.19 mmol) in DMF (5 mL) at 0° C. The mixture was stirred at room temperature for 2 hours. Iodobutane (0.15 mL, 1.31 mmol) was added and stirred for 8 hours. The reaction was diluted with ethyl acetate. The organic layer was washed with water, dried over Na$_2$SO$_4$, concentrated under reduced pressure and purified by MPLC to obtain Compound 12d in a yield of 79% yield. R$_f$=0.33 (3:7=ethyl acetate:hexane).

$^1$H NMR (500 MHz, CDCl$_3$) δ 8.39 (t, J=1.5 Hz, 1H), 8.17 (td, J=7.5 Hz, 1.5 Hz, 1H), 7.95 (td, J=8.0 Hz, 1.5 Hz, 1H), 7.83-7.81 (m, 1H), 7.60 (t, J=8.0 Hz, 1H), 7.43-7.41 (m, 1H), 7.32-7.28 (m, 2H), 4.23 (t, J=7.5 Hz, 2H), 3.93 (s, 3H), 1.84-1.78 (m, 2H), 1.31-1.24 (m, 2H), 0.85 (t, J=7.5 Hz, 3H). $^{13}$C NMR (125 MHz, CDCl$_3$) δ 166.4, 152.5, 143.1, 135.7, 133.9, 131.1, 130.8, 130.7, 130.2, 129.1, 123.0, 122.7, 120.1, 110.3, 52.4, 44.7, 31.9, 20.0, 13.6. ESI MS (m/e) 309.16 [M+H]$^+$.

(3-6) Compound 13: 3-(1H-benzo[d]amidazol-2-yl)-N-hydroxybenzamide

Hydroxylamine hydrochloride (3.72 g, 53.51 mmol) in methanol (5 mL) was added to a solution of potassium hydroxide (3.00 g, 53.51 mmol) in methanol (5 mL) at 0° C. The mixture was stirred at 0° C. for 15 minutes and the precipitated potassium chloride was removed and the filtrate was used as such; To a solution of compound 11 (0.3 g, 11.89 mmol) in tetrahydrofuran (10 mL) was added to freshly prepared hydroxylamine at 0° C. and stirred at the same temperature for 3 hours. The mixture was neutralized to pH 7 with 3N HCl and extracted with ethyl acetate. The organic layer was dried over Na$_2$SO$_4$, concentrated under reduced pressure and purified by MPLC to obtain Compound 13 in a yield of 33%.

$^1$H NMR (500 MHz, DMSO-D$_6$) δ 10.12 (brs, 2H), 8.91 (s, 1H), 8.72 (d, J=8.5 Hz, 1H), 8.22 (d, J=8.0 Hz, 1H), 7.86-7.83 (m, 3H), 7.56-7.54 (m, 2H). $^{13}$C NMR (125 MHz, CD$_3$OD) δ 167.5, 149.5, 135.4, 133.9, 133.0, 131.5, 132.8, 129.9, 127.9, 124.2, 115.1. ESI MS (m/e) 254.09 [M+H]$^+$.

(3-7) Compound 14a: N-hydroxy-3-(1-methyl-1H-benzo[d]imidazol-2-yl)benzamide Hydroxylamine hydrochloride (3.72 g, 53.51 mmol) in methanol (5 mL) was added to a solution of potassium hydroxide (3.00 g, 53.51 mmol) in methanol (5 mL) at 0° C. The mixture was stirred at 0° C. for 15 minutes and the precipitated potassium chloride was removed and the filtrate was used as such; To a solution of compound 12a (0.30 g, 11.89 mmol) in tetrahydrofuran (10 mL) was added to freshly prepared hydroxylamine at 0° C. and stirred at the same temperature for 3 hours. The mixture was neutralized to pH 7 with acetic acid and extracted with ethyl acetate. The organic layer was dried over Na$_2$SO$_4$, concentrated under reduced pressure and purified by MPLC to obtain Compound 14a in a yield of 49%.

$^1$H NMR (500 MHz, DMSO-D$_6$) δ 11.4 (s, 1H), 9.24 (s, 1H), 8.23 (s, 1H), 8.01 (d, J=8 Hz, 1H), 7.94 (d, J=8.5 Hz, 1H), 7.71-7.62 (m, 4H), 7.33 (m, 2H), 3.90 (s, 3H) $^{13}$C NMR (125 MHz, DMSO-D$_6$) δ 163.6, 152.4, 142.5, 136.5, 133.3, 131.9, 130.4, 129.0, 128.1, 127.7, 122.6, 122.2, 119.1, 110.8, 31.8. ESI MS (m/e) 268.11 [M+H]$^+$.

(3-8) Compound 14b: 3-(1-Ethyl-1H-benzo[d]imidazol-2-yl)-N-hydroxybenzamide

Hydroxylamine hydrochloride (3.72 g, 53.51 mmol) in methanol (5 mL) was added to a solution of potassium hydroxide (3.00 g, 53.51 mmol) in methanol (5 mL) at 0° C. The mixture was stirred at 0° C. for 15 minute and the precipitated potassium chloride was removed and the filtrate was used as such, To a solution of compound 12b (0.30 g, 11.89 mmol) in tetrahydrofuran (10 mL) was added to freshly prepared hydroxylamine at 0° C. and stirred at the same temperature for 3 hours. The mixture was neutralized to pH 7 with 3N HCl and extracted with ethyl acetate. The organic layer was dried over Na$_2$SO$_4$, concentrated under reduced pressure and purified by MPLC to obtain Compound 14b in a yield of 43%.

$^1$H NMR (500 MHz, DMSO-D$_6$) δ 8.33 (s, 1H), 8.12 (d, J=8 Hz, 1H), 8.03 (d, J=8 Hz, 1H), 7.74-7.67 (m, 3H), 7.33-7.25 (m, 2H), 4.33 (q, J=7 Hz, 2H), 1.36 (t, J=7 Hz, 3H) $^{13}$C NMR (125 MHz, CD$_3$OD) δ 168.4, 152.5, 141.9, 135.0, 132.9, 131.0, 130.0, 129.9, 128.9, 123.2, 122.7, 118.5, 39.4, 14.1. ESI MS (m/e) 282.12 [M+H]$^+$.

(3-9) Compound 14c: N-hydroxy-3-(1-propyl-1H-benzo[d]imidazol-2-yl)benzamide Hydroxylamine hydrochloride (2.83 g, 40.71 mmol) in methanol (5 mL) was added to a solution of potassium hydroxide (2.28 g, 40.71 mmol) in methanol (5 mL) at 0° C. The mixture was stirred at 0° C. for 15 minutes and the precipitated potassium chloride was removed and the filtrate was used as such; To a solution of compound 12c (0.28 g, 0.90 mmol) in tetrahydrofuran (10 mL) was added to freshly prepared hydroxylamine at 0° C. and stirred at the same temperature for 3 hours. The mixture was neutralized to pH 7 with acetic acid and extracted with ethyl acetate. The organic layer was dried over Na$_2$SO$_4$, concentrated under reduced pressure and purified by MPLC to obtain Compound 14c in a yield of 55%. R$_f$=0.22 (8:2=ethyl acetate:hexane).

$^1$H NMR (500 MHz, DMSO-D$_6$) δ 11.39 (s, 1H), 9.14 (s, 1H), 8.09 (s, 1H), 7.89 (d, J=6.5 Hz, 2H), 7.67-7.62 (m, 3H), 7.28-7.21 (m, 2H), 4.25 (t, J=7.5 Hz, 2H), 1.66 (q, J=6.5 Hz, 2H), 0.69 (t, J=7.0 Hz, 3H). $^{13}$C NMR (125 MHz, DMSO-Ds) δ 163.5, 152.3, 142.6, 135.8, 133.2, 131.7, 131.2, 129.1, 128.2, 127.6, 122.6, 122.1, 119.3, 111.1, 45.6, 22.7, 11.0. ESI MS (m/e) 296.13 [M+H]$^+$.

(3-10) Compound 14d: 3-(1-Butyl-1H-benzo[d]imidazol-2-yl)-N-hydroxybenzamide Hydroxylamine hydrochloride (2.83 g, 40.71 mmol) in methanol (5 mL) was added to a solution of potassium hydroxide (2.28 g, 40.71 mmol) in methanol (5 mL) at 0° C. The mixture was stirred at 0° C. for 15 minutes and the precipitated potassium chloride was removed and the filtrate was used as such; To a solution of compound 12d (0.28 g, 0.90 mmol) in tetrahydrofuran (10 mL) was added to freshly prepared hydroxylamine at 0° C. and stirred at the same temperature for 3 hours. The mixture was neutralized to pH 7 with acetic acid and extracted with ethyl acetate. The organic layer was dried over Na$_2$SO$_4$, concentrated under reduced pressure and purified by MPLC to obtain Compound 14d in a yield of 50%. R$_f$=0.28 (8:2=ethyl acetate: hexane).

$^1$H NMR (500 MHz, DMSO-D$_6$) δ 11.45 (s, 1H), 9.21 (s, 1H), 8.15 (t, J=1.5 Hz, 1H), 7.95-7.92 (m, 2H), 7.71-7.66 (m, 3H), 7.33-7.25 (m, 2H), 4.32 (t, J=7.5 Hz, 2H), 1.69-1.63 (m, 2H), 1.18-1.10 (m, 2H), 0.74 (t, J=7.5 Hz, 3H). $^{13}$C NMR (125 MHz, DMSO-D$_6$) δ 163.4, 152.3, 142.6, 135.7, 133.3, 131.7, 130.8, 129.0, 128.0, 127.6, 122.7, 122.1, 119.3, 111.1, 43.8, 31.3, 19.2, 13.3. ESI MS (m/e) 310.15 [M+H]$^+$.

[Example 4] Compound Synthesis (17a-b)

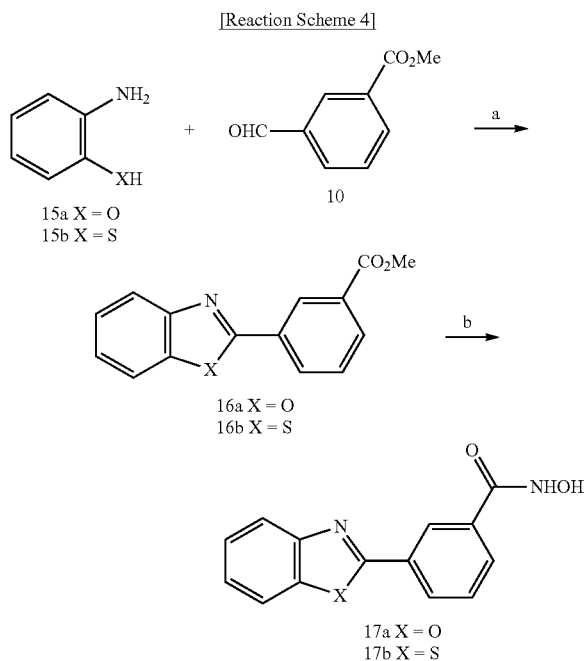

Reaction Scheme 4 shows the synthesis process of Compounds 17a-17b.

In Reaction Scheme 4, unlike Reaction Scheme 2, the first attempt to construct Compounds 16a-16b through iodine-mediated cyclization of Compounds 15a-15b with aldehyde 10 was not good. Thus, sodium cyanide-catalyzed cyclization of Compounds 15a-15b with aldehyde 10 was performed in DMF and Compounds 16a-16b were successfully obtained in yields of 44-67%. Finally, Compounds 16a-16b were converted to Compounds 17a-17b with NH$_2$OH and KOH in methanol. In more detail, the process was performed as follows.

(4-1) Compound 16a: Methyl 3-(benzo[d]oxazol-2-yl)benzoate

2-Aminophenol (0.50 g, 4.58 mmol) and methyl 3-formylbenzoate (0.75 g, 4.58 mmol) in 40 mL of DMF were added to a molecular sieve (molecular filter). Then, the reaction mixture was stirred at 60° C. for 4 hours under open flask. After 4 hours, the reaction mixture was cooled at room temperature and added to sodium cyanide (NaCN, 0.02 g, 0.46 mmol). The reaction mixture was stirred at room temperature for 24 hours. The mixture was concentrated under reduced pressure and purified by a column to obtain Compound 16a in a yield of 67%. R$_f$=0.25 (1:9=ethyl acetate:hexane).

$^1$H NMR (500 MHz, DMSO-D$_6$) δ 8.70 (s, 1H), 8.43 (d, J=8.5 Hz, 1H), 8.17 (d, J=8.0 Hz, 1H), 7.84-7.82 (m, 2H), 7.77 (t, J=7.5 Hz 1H), 7.48-7.41 (m, 2H), 3.92 (s, 1H). $^{13}$C NMR (125 MHz, CDCl$_3$) δ 166.3, 162.2, 150.9, 142.1, 132.5, 131.8, 131.2, 129.3, 128.8, 127.7, 125.6, 124.9, 120.3, 52.5. ESI MS (m/e) 254.08 [M+H]$^+$.

(4-2) Compound 16b: Methyl 3-(benzo[d]thiazol-2-yl)benzoate

2-Aminothiophenol (0.50 g, 4.58 mmol) and methyl 3-formylbenzoate (0.66 g, 4.58 mmol) in 40 mL of DMF were added to a molecular sieve (molecular filter). Then, the reaction mixture was stirred at 60° C. for 4 hours under open flask. After 4 hours, the reaction mixture was cooled at room temperature and added to sodium cyanide (0.02 g, 0.46 mmol). The reaction mixture was stirred at room temperature for 24 hours. The mixture was concentrated under reduced pressure and purified by a column to obtain Compound 16b in a yield of 44%. R$_f$=0.26 (1:9=ethyl acetate: hexane).

$^1$H NMR (500 MHz, DMSO-D$_6$) δ 8.57 (s, 1H), 8.26 (d, J=7.5 Hz, 1H), 8.13 (d, J=7.5 HZ, 1H), 8.08 (d, J=8.5 Hz, 2H), 7.68 (t, J=7.5 Hz, 1H), 7.55 (t, J=8.0 Hz, 1H), 7.46 (t, J=8.0 Hz, 1H), 3.90 (s, 3H). $^{13}$C NMR (125 MHz, CDCl$_3$) δ 166.8, 166.4, 154.1, 135.1, 134.0, 131.8, 131.6, 131.1, 129.2, 128.6, 126.5, 126.5, 125.5, 123.4, 52.4. ESI MS (m/e) 270.06 [M+H]$^+$.

(4-3) Compound 17a: 3-(Benzo[d]oxazol-2-yl)-N-hydroxybenzamide

Hydroxylamine hydrochloride (3.70 g, 53.31 mmol) in methanol (6 mL) was added to a solution of potassium hydroxide (2.99 g, 53.31 mmol) in methanol (6 mL) at 0° C. The mixture was stirred at 0° C. for 15 minutes, the precipitated potassium chloride was removed and the filtrate was used as such, To a solution of compound 16a (0.30 g, 1.18 mmol) in tetrahydrofuran (12 mL) was added to the newly prepared hydroxylamine at 0° C. and stirred at the same temperature for 3 hours. The mixture was neutralized to pH 7 with 3N HCl and extracted with ethyl acetate. The organic layer was dried over Na$_2$SO$_4$, concentrated under reduced pressure and purified by MPLC to obtain Compound 17a in a yield of 50%.

$^1$H NMR (500 MHz, DMSO-D$_6$) δ 11.52 (s, 1H), 9.24 (s, 1H), 8.61 (s, 1H), 8.33 (d, J=7.5 Hz, 1H), 8.0 (d, J=8.0 Hz, 1H), 7.83 (t, J=8.0 Hz, 2H), 7.71 (t, J=8.0 Hz, 1H), 7.46-7.43 (m, 2H). $^{13}$C NMR (125 MHz, DMSO-D$_6$) δ 163.2, 161.7, 150.3, 141.4, 133.8, 130.1, 129.4, 129.7, 126.7, 125.9, 125.1, 120.0, 111.1. ESI MS (m/e) 255.08 [M+H]$^+$.

(4-4) Compound 17b: 3-(benzo[d]thiazol-2-yl)-N-hydroxybenzamide

Hydroxylamine hydrochloride (2.32 g, 33.42 mmol) in methanol (6 mL) was added to a solution of potassium hydroxide (1.87 g, 33.42 mmol) in methanol (6 mL) at 0° C. The mixture was stirred at 0° C. for 15 minutes, the precipitated potassium chloride was removed and the filtrate was used as such, To a solution of compound 16b (0.20 g, 0.74 mmo) in tetrahydrofuran (12 mL) was added to the newly prepared hydroxylamine at 0° C. and stirred at the same temperature for 3 hours. The mixture was neutralized to pH 7 with 3N HCl and extracted with ethyl acetate. The organic layer was dried over $Na_2SO_4$, concentrated under reduced pressure and purified by MPLC to obtain Compound 17b in a yield of 4%.

$^1$H NMR (500 MHz, DMSO-$D_6$) δ 11.51 (s, 1H), 8.47 (s, 1H), 8.24 (d, J=8.0 Hz, 1H), 8.20 (d, J=7.5 Hz, 1H), 8.11 (d, J=8.0 Hz, 1H), 7.94 (d, J=7.5 Hz, 1H), 7.67 (t, J=7.5 Hz, 1H), 7.58 (t, J=7.0 Hz, 1H), 7.50 (t, J=7.0 Hz, 1H). $^{13}$C NMR (125 MHz, DMSO-$D_6$) δ 166.6, 163.3, 153.5, 134.6, 133.9, 133.1, 129.8, 129.7, 129.6, 126.9, 125.8, 125.6, 123.1, 122.6. ESI MS (m/e) 271.05 $[M+H]^+$.

[Experimental Example 1] Anti-Proliferative Effect in SH-SY5Y Cell Line

Anti-proliferative activity against human neuroblastoma cell line SH-SY5Y, an in vitro model of human malignant metastatic neuroblastoma, was investigated using the compounds synthesized through the above Examples 1 to 4.

1. Cell Culture

SH-SY5Y cells were cultured in DMEM (Dulbecco's Modified Eagle's Media) with L-glutamine supplemented with 500 mg/mL of streptomycin, 100 units/mL of penicillin and 10% fetal bovine serum (FBS). The cells were grown to confluence in a humidified atmosphere (37° C., 5% $CO_2$).

2. Experiment Result

Table 1 below is a result of the anti-proliferative activity experiment according to Experimental Example 1, and shows the cytotoxicity value for the cell line SH-SY5Y after 72 hours, i.e., the maximum concentration value at the moment when the proliferation of cells is reduced by half by the compound ($GI_{50}$; Half maximal growth inhibition concentration).

TABLE 1

| Compound | R | *SH-SY5Y ($GI_{50}$; μM) | Compound | R | SH-SY5Y ($GI_{50}$; μM) |
|---|---|---|---|---|---|
| 5 | N—H | 60 | 13 | N—H | >100 |
| 6a | N—Me | 58.3 | 14a | N—Me | >100 |
| 6b | N—Et | 38.1 | 14b | N—Et | 28.2 |
| 6c | N—Pr | 54.7 | 14c | N—Pr | 34.6 |
| 6d | N—Bu | 26.8 | 14d | N—Bu | 20.7 |
| 9a | O | 25.7 | 17a | O | 17.5 |
| 9b | S | 2.01 | 17b | S | 21.4 |
| SAHA | | 2.90 | | | |

Referring to Table 1, Compound 9b exerted the most potent anti-proliferative activity with a $GI_{50}$ value of 2.01 μM against SH-SY5Y cell line. The reference drug SAHA also furnished good anti-proliferative activity with a $GI_{50}$ value of 2.90 μM against the SH-SY5Y cell line. The SAHA is a drug used to treat cutaneous T cell lymphoma, which is a type of cancer.

Para-substituted benzimidazole analogues 5 and 6a-6d show relatively low anti-proliferative activity with $GI_{50}$ values of 38.1-60 μM compared to benzothiazole analogue Compound 9b, but the longer butyl substituent on nitrogen atom of benzimidazole group (6d) showed an increased anti-proliferative activity with a $GI_{50}$ value of 26.8 μM. Benzoxazole 9a, which has an oxygen atom replacing sulfur atom of the most potent Compound 9b, has a $GI_{50}$ value of 25.7 μM, furnished 12-fold less potent anti-proliferative activity than Compound 9b. This is probably because the hydrophobicity of sulfur atom plays a critical role in binding to HDAC enzymes and in cell permeability.

Ethyl, propyl and butyl substituents on the nitrogen atom of the meta-substituted benzimidazole moiety, including Compounds 14b-14d also have increased cellular anti-proliferative activity against SH-SY5Y cell line, compared to methyl substituted Compound 13 and non-substituted Compound 14a. However, all meta-substituted Compounds 13, 14a-14d and 17a-17b showed relatively poor or moderate anti-proliferative activity, compared to para-substituted benzothiazole 9b.

[Experimental Example 2] Anti-Proliferative Effect in Breast Cancer Cell Line MDA-MB-231

Anti-proliferative activity against breast cancer cell line MDA-MB-231 was investigated using the compounds synthesized through the above Examples 1 to 4.

Table 2 below shows the results according to the anti-proliferative activity test for the breast cancer cell line MDA-MB-231. Referring to Table 2, Compound 9b showed the strongest anti-proliferative activity with a $GI_{50}$ value of 3.86 μM against the MDA-MB-231 cell line, and the reference drug SAHA also showed excellent anti-proliferative activity with a $GI_{50}$ value of 3.16 μM against the MDA-MB-231 cell line. Benzoxazole 9a, which has an oxygen atom instead of sulfur atom of the most potent compound 9b, has a $GI_{50}$ value of 8.31 μM, which is less potent than Compound 9b, but provides high anti-proliferative activity.

TABLE 2

| Compound | R | MDA-MB-231 ($GI_{50}$; μM) | Compound | R | MDA-MB-231 ($GI_{50}$; μM) |
|---|---|---|---|---|---|
| 5 | N—H | 15.6 | 13 | N—H | >100 |
| 6a | N—Me | 40.3 | 14a | N—Me | >100 |
| 6b | N—Et | 15.6 | 14b | N—Et | >100 |
| 6c | N—Pr | 44.6 | 14c | N—Pr | 62.1 |
| 6d | N—Bu | 35.5 | 14d | N—Bu | 60.8 |
| 9a | O | 8.31 | 17a | O | 47.9 |
| 9b | S | 3.86 | 17b | S | 23.1 |
| SAHA | | 3.16 | | | |

[Experimental Example 3] Anti-Proliferative Effect of Compound 9b in H1975, A549 and HeLa Cell Lines Anti-proliferative activity against non-small cell lung cancer cell line H1975, lung cancer cell line A549 and cervical cancer cell line HeLa was investigated by using Compound 9b, which showed high anti-proliferative activity in the above Experimental Examples 1 and 2.

TABLE 3

| Compound | H1975 ($GI_{50}$; μM) | A549 ($GI_{50}$; μM) | HeLa ($GI_{50}$; μM) |
|---|---|---|---|
| 9b | 3.71 | 15.6 | 13.5 |

Table 3 shows the results of the anti-proliferative activity test for the non-small cell lung cancer cell line H1975, the lung cancer cell line A549, and the cervical cancer cell line HeLa. Referring to Table 3, Compound 9b generally provides high anti-proliferative activity against the cell lines and it can be confirmed that it exhibits anti-proliferative effect in various cancer cell lines.

[Experimental Example 4] Colony Formation Analysis

Anchorage-independent cell growth is a characteristic of cell carcinogenesis and indicates the ability of transformed cells to grow independently of a solid surface. The soft agar colony formation assay is a widely used method to measure the capability of anchorage-independent cell growth in vitro. Thus, the suppressive effect of Compound 9b on Anchorage-independent cell growth by soft agar colony formation assay.
1. Experimental Method SH-SY5Y cells were seeded in a 6-well plate with 1.2% agar ($4\times10^5$ cells/well) and Compound 9b was added at concentrations of 1 μM, 3 μM and 5 μM and cultured for 1-2 weeks. DMSO (0.5%) was used as a negative control. After incubation, colonies were stained using by 0.05% crystal violet for 10 minutes. The colonies were washed by 3rd distilled water and captured.
2. Experiment Result FIG. 2 shows the inhibitory effect of Compound 9b according to an experimental example of the present invention. Referring to FIG. 2, treatment of SH-SY5Y cells with Compound 9b showed an inhibitory effect on colony formation of SH-SY5Y neuroblastoma. In addition, the ability of SH-SY5Y cells to form colonies decreased in a dose-dependent manner as the concentration of Compound 9b increased, and the anchorage-independent cell growth of SH-SY5Y neuroblastoma was almost completely inhibited at the concentration of 3 μM of Compound 9b. Overall, the experimental data showed that Compound 9b effectively inhibited the anchorage-independent growth capacity of SH-SY5Y cells in a concentration-dependent manner.

Hereinafter, a preparation example of a composition containing the Compound 9b according to the present invention will be described, but the present invention is not intended to limit it, but is intended to be described in detail.

[Prescription Example 1] Prescription Example of Pharmaceutical Composition

[Prescription Example 1-1] Preparation of Powder

Powder was prepared by mixing 20 mg of Compound 9b, 100 mg of lactose and 10 mg of talc and filling in an airtight bag.

[Prescription Example 1-2] Preparation of Tablets

Tablets were prepared by mixing 20 mg of Compound 9b, 100 mg of corn starch, 100 mg of lactose and 2 mg of magnesium stearate and tableting according to a conventional tablet preparation method.

[Prescription Example 1-3] Preparation of Capsule

A capsule was prepared by mixing 10 mg of Compound 9b, 100 mg of corn starch, 100 mg of lactose and 2 mg of magnesium stearate and filling the above components in a gelatin capsule according to a conventional capsule preparation method.

[Prescription Example 1-4] Preparation of Injection

Injections were prepared by mixing 10 mg of Compound 9b, an appropriate amount of sterile distilled water for injection and an appropriate amount of a pH adjuster and processing the above components per ampoule (2 ml) according to a conventional preparation method for injection.

[Prescription Example 1-5] Preparation of Ointment

An ointment was prepared by mixing 10 mg of Compound 9b, 250 mg of PEG-4000, 650 mg of PEG-400, 10 mg of white Vaseline, 1.44 mg of methyl p-hydroxybenzoate, 0.18 mg of propyl p-hydroxybenzoate and the remaining amount of purified water and processing the above components according to a conventional ointment preparation method.

[Prescription Example 2] Health Functional Food

[Prescription Example 2-1] Manufacture of Health Food

Compound 9b of 1 mg, appropriate amount of vitamin mixture (vitamin A acetate of 70 μg, vitamin E of 1.0 mg, vitamin B1 of 0.13 mg, vitamin B2 of 0.15 mg, vitamin B6 of 0.5 mg, vitamin B12 of 0.2 μg, vitamin C of 10 mg, biotin of 10 μg, nicotinic acid amide of 1.7 mg, folic acid of 50 μg, calcium pantothenate of 0.5 mg) and an appropriate amount of inorganic mixture (ferrous sulfate of 1.75 mg, zinc oxide of 0.82 mg, magnesium carbonate of 25.3 mg, potassium dihydrogen phosphate of 15 mg, dicalcium phosphate of 55 mg, potassium citrate of 90 mg, calcium carbonate of 100 mg, magnesium chloride of 24.8 mg) were mixed, and then granules were prepared to prepare health food according to a conventional method.

[Prescription Example 2-2] Preparation of Health Drink

Compound 9b of 1 mg, citric acid of 1000 mg, oligosaccharide of 100 g, plum concentrate of 2 g, taurine of 1 g and purified water were mixed so that the total amount was 900 ml and the above ingredients were mixed according to a conventional health drink manufacturing method, stirred with heating at 85° C. for about 1 hour, and the resulting solution was filtered and added in a sterilized 2 L container, sealed and sterilized, and then stored in a refrigerator.

So far, the present invention was investigated by specific examples of the present invention. Those of ordinary skill in the art to which the present invention pertains could understand that the present invention may be implemented in a modified form without departing from the essential characteristics of the present invention. Therefore, the disclosed embodiments should be considered from an explanatory point of view rather than a limitative point of view. The scope of the present invention is shown in the claims rather than the above description, and all differences within the scope equivalent thereto should be construed as being included in the present invention.

The invention claimed is:

1. A compound represented by Chemical Formula 1 or a pharmaceutically acceptable salt thereof:

[Chemical Formula 1]

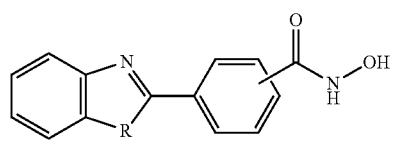

wherein R is O or S.

2. The compound or a pharmaceutically acceptable salt thereof of claim 1, wherein the compound is selected from the group consisting of 4-(benzo[d]oxazol-2-yl)-N-hydroxybenzamide, 4-(benzo[d]thiazol-2-yl)-N-hydroxybenzamide, 3-(benzo[d]oxazol-2-yl)-N-hydroxybenzamide and 3-(benzo[d]thiazol-2-yl)-N-hydroxybenzamide.

3. A pharmaceutical composition for treating cancer disease comprising the compound or a pharmaceutically acceptable salt thereof of claim 1 as an active ingredient.

4. The pharmaceutical composition for treating cancer diseases of claim 3, wherein the cancer disease is selected from the group consisting of brain cancer, breast cancer, lung cancer, skin cancer, ovarian cancer, uterine cancer, prostate cancer, kidney cancer, colon cancer, pancreatic cancer, gastric cancer, liver cancer, colon cancer, head or neck cancer, laryngeal cancer, esophageal cancer, blood cancer and leukemia.

5. A pharmaceutical composition for treating cancer disease comprising the compound or a pharmaceutically acceptable salt thereof of claim 2 as an active ingredient.

6. The pharmaceutical composition for treating cancer diseases of claim 5, wherein the cancer disease is selected from the group consisting of brain cancer, breast cancer, lung cancer, skin cancer, ovarian cancer, uterine cancer, prostate cancer, kidney cancer, colon cancer, pancreatic cancer, gastric cancer, liver cancer, colon cancer, head or neck cancer, laryngeal cancer, esophageal cancer, blood cancer and leukemia.

* * * * *